US007030073B2

(12) United States Patent
McCammon

(10) Patent No.: US 7,030,073 B2
(45) Date of Patent: Apr. 18, 2006

(54) CHEMICAL COMPOSITION

(76) Inventor: Donald L. McCammon, 8270 Mara Vista Ct., Orlando, FL (US) 32827

( * ) Notice: Subject to any disclaimer, the term of this patent is extended or adjusted under 35 U.S.C. 154(b) by 206 days.

(21) Appl. No.: 10/666,187

(22) Filed: Sep. 17, 2003

(65) Prior Publication Data

US 2004/0063594 A1    Apr. 1, 2004

Related U.S. Application Data

(60) Provisional application No. 60/414,038, filed on Sep. 27, 2002.

(51) Int. Cl.
 *C11D 3/44* (2006.01)
 *C11D 3/18* (2006.01)
 *C11D 7/50* (2006.01)

(52) U.S. Cl. .............. 510/138; 510/139; 510/158; 510/208; 510/209; 510/213; 510/365; 510/404

(58) Field of Classification Search ............... 510/138, 510/139, 158, 159, 208, 209, 213, 365, 404, 510/407
See application file for complete search history.

(56) References Cited

U.S. PATENT DOCUMENTS

| 3,036,024 A | * | 5/1962 | Post et al. ................ 524/479 |
| 3,920,415 A | | 11/1975 | Reusser et al. ............. 44/424 |
| 4,043,765 A | | 8/1977 | Tanner ........................ 44/519 |
| 4,113,677 A | * | 9/1978 | Svedas et al. ............... 524/277 |
| 4,155,870 A | * | 5/1979 | Jorgensen .................. 510/139 |
| 4,693,840 A | * | 9/1987 | Trinh et al. ................. 510/242 |
| 4,718,942 A | * | 1/1988 | Laura et al. .............. 106/14.29 |
| 4,810,291 A | * | 3/1989 | Osberghaus et al. .......... 106/10 |
| 5,226,405 A | | 7/1993 | Snow ......................... 126/258 |
| 5,616,746 A | * | 4/1997 | Mahieu et al. ................ 554/66 |
| 5,665,333 A | * | 9/1997 | Homola et al. .............. 424/54 |
| 5,962,074 A | * | 10/1999 | Wollner ..................... 427/322 |
| 6,093,224 A | | 7/2000 | Jones ........................ 44/502 |
| 6,193,791 B1 | * | 2/2001 | Vander Louw et al. ......... 106/3 |
| 6,235,824 B1 | * | 5/2001 | Vander Louw et al. ..... 524/278 |

FOREIGN PATENT DOCUMENTS

| FR | 2640277 | * | 6/1990 |
| GB | 894112 | * | 4/1962 |
| SU | 907044 | * | 2/1982 |

* cited by examiner

*Primary Examiner*—Lorna M. Douyon
(74) *Attorney, Agent, or Firm*—William M. Hobby, III

(57) ABSTRACT

A process for making a chemical composition includes the steps of mixing 200–800 parts by volume of petroleum solvent with 10–500 parts by volume of normal paraffin or isoparaffin at room temperature to form a solvent paraffin mixture. A microcrystalline wax is heated to between 180–200 degrees Fahrenheit until melted and 90–700 parts by volume of melted microcrystalline wax is vigorously mixed with the normal paraffin or isoparaffin mixture to form a creamy liquid useful as a hand cleaner and paint remover as well as a fire starter.

10 Claims, No Drawings

CHEMICAL COMPOSITION

This application claims the benefit of U.S. provisional application Ser. No. 60/414,038, filed Sep. 27, 2002.

FIELD OF THE INVENTION

This invention relates to a chemical composition and more particularly to a microcrystalline wax composition for binding a petroleum solvent so as to result in a creamy smooth product with a variety of applications.

BACKGROUND OF THE INVENTION

Hydrocarbons are chemical compounds of hydrogen and carbon, also referred to as organic compounds. Carbon atoms form the skeleton of the hydrocarbon molecule and may be arranged in chains (aliphatic) or rings (cyclic). There are three principal types of hydrocarbons that occur naturally in petroleum: paraffins, naphthenes and aromatics. Paraffins are aliphatic, while the other two are cyclic.

The most common petroleum solvents are mineral spirits, xylene, toluene, hexane, heptane, and napthas. Aromatic-type solvents have the highest solvency for organic chemical materials, followed by napthenes and paraffins. In most chemical compositions comprising solvents, the solvent disappears, usually by evaporation, after it has served its purpose. Some solvents, particularly aromatics, pose serious physical and health hazards.

Petroleum solvents have multiple industrial and home applications and are used in paints, adhesives, as paint thinners, paint strippers, aerosol sprays, dry-cleaning fluid, charcoal lighter, degreasers, nail polish removers, and are present in textiles, plastics, waxes and many other products. Liquid petroleum solvents are highly volatile, which makes them a fire hazard, as well as a health hazard due to their rapid evaporation rates, inhalation or exposure risks, and disposal problems.

Petroleum wax is a relatively high molecular-weight hydrocarbon (approximately C16 to C50), solid at room temperature and derived from higher boiling petroleum fractions. There are three general types of petroleum-derived wax: paraffin, microcrystalline and petrolatum. Microcrystalline waxes differ in that the crystal structure is more branched and the carbon chains are longer. Microcrystalline waxes are typically more flexible and have higher tensile strengths and melting points. They are also more adhesive and bind with solvents. When used in chemical compounds, microcrystalline waxes are typically ground up into micronized particles and combined with water or solvents as emulsions or dispersions.

In order to reduce the risk of use in handling of petroleum solvents, the present invention includes a method of mixing petroleum solvents into a stable composition that is less volatile and less of a hazard, yet still has multiple applications.

Prior art U.S. patents petroleum solvents and paraffins include Tanner, U.S. Pat. No. 4,043,765, dated Aug. 23, 1977 for Artificial Fireplace Logs with Ignition Strips. Tanner describes that a suitable thickener may be mixed with a fuel to form a paste and lists a variety of useful thickeners. The thickener may be added to the fuel with the use of heat as an aid in formation of the paste. U.S. Pat. No. 5,226,405 to Snow dated Jul. 13, 1993 is for an Ignition Platform and Fuel Component for Kindling a Fire. Snow uses a fuel composition for impregnating an ignition platform to be used to rapidly ignite coal or charcoal fires or wood in a fireplace. In his composition, Snow includes polyethylene terephthalate (PET) hydrocarbons in a specified range along with a low melt paraffin and microcrystalline wax and may include refined petroleum. Snow describes this composition as burning clean, substantially without smoke, and to be essentially non-volatile, safe to store and transport, and easy to pack and handle.

U.S. Pat. No. 3,920,415 dated Nov. 18, 1975 to Reusser et al. is for Odor Inhibition for Paraffin Hydrocarbons. This patent describes that "odorless mineral spirits" are generally marketed for use as paint thinner, insecticide carrier oil, charcoal lighter fluid, industrial cleaning compounds and general solvents. This invention relies on the addition of 2,4,6-tris-(dimethyl aminomethyl) phenol to inhibit the oxidation of odorless mineral spirits with consequent prevention of odor formation. The Jones U.S. Pat. No. 6,093,224 of Jul. 25, 2000 is for a Long Burning Fire Starter. The Jones composition comprises odorless mineral spirits and propylene glycol, which are used to saturate a holder made of a mix of diatomaceous earth and wood pellets. Once impregnated with the fuel composition, the holder is overcoated with paraffin wax.

The following illustrates the principles, practice, and applications of methods constituting this invention. While this invention is satisfied by embodiments in many different forms, there will herein be described in detail certain embodiments of the invention with the understanding that the present disclosure is to be considered as exemplary of the principles of the invention and is not intended to limit the invention to the embodiments illustrated and described.

SUMMARY OF THE INVENTION

A process for making a chemical composition includes the steps of mixing 200–800 parts by volume of petroleum solvent with 10–500 parts by volume of normal paraffin or isoparaffin at room temperature to form a solvent paraffin mixture. A microcrystalline wax is heated to between 180–200 degrees Fahrenheit until melted and 90–700 parts by volume of a melted microcrystalline wax are vigorously mixed with the liquid paraffin and solvent mixture to form a creamy liquid useful as a hand cream and paint remover as well as a fire starter. The hand cream paint remover may have from 400–800 parts by volume of liquid petroleum solvent mixed with 10–200 parts by volume of normal paraffin or isoparaffin and 150–200 parts by volume of microcrystalline wax and further mixed with about 1–20 parts by volume of an ionic surfactant and may include 1–10 parts by volume of aloe oil and 1–10 parts by volume of eucalyptus oil.

DESCRIPTION OF THE PREFERRED EMBODIMENTS

Microcrystalline wax has unique molecular structure which allows it to bind petroleum solvents. At room temperature, however, microcrystalline wax does not readily combine with petroleum solvents, requiring that the wax be pulverized into small pieces in order to create a solvent-borne wax dispersion. The particle size of the wax in the dispersion is typically greater than one micron.

It has been discovered that melting the microcrystalline wax and pouring it into the solvent while mixing, allows the wax to readily bind to the solvent. Trial and error has shown there must be a sufficient liquid microcrystalline wax-to-solvent ratio in order to bind all of the solvent, resulting in a stable composition that does not separate. For example, this minimum ratio for microcrystalline wax and synthetic mineral spirits is approximately one part wax to four parts of mineral spirits. The resultant combination is a creamy composition that is less volatile and less hazardous than the solvent alone. Additional melted microcrystalline wax increases the thickness of the composition as the mixture increases in wax content. It has also been found that when using a minimal amount of wax to solvent, the resulting composition has waxy lumps. These lumps may be eliminated by adding white oil, isoparaffin or normal paraffin to the mixture, which results in a smoother consistency.

Typical Applications of the Inventive Composition:

The resultant compound has applications by itself, such as a carbonaceous fire lighter or hand cleaner and paint remover. The composition may also be the base stock for other products when combined with various additives. A thicker version of the composition comprising pumice, a surfactant, and hand emollients results in an effective hand cream/paint remover for oil based paint. Further, the composition can be combined with crushed coal or coal dust for use as a fuel.

The solvent that is bound in the composition becomes less volatile and less hazardous and the composition may be used as a base stock for additives to create multiple consumer products.

EXAMPLE 1

The following example is provided to illustrate one method of preparation of the inventive composition, however, those skilled in the art will recognize that other petroleum solvents may be used as well, instead of that presented in the example.

Starting with 200 to 800 parts of a synthetic isoparaffinic hydrocarbon, sometimes otherwise referred to as odorless mineral spirit, at room temperature, add 10 to 500 parts of liquid (normal paraffin or isoparaffin) at room temperature and mix vigorously. Heat microcrystalline wax at approximately 180 to 200 degrees Fahrenheit, until it is completely melted. Pour 90 to 700 parts of the melted microcrystalline wax into the solvent and liquid paraffin mixture, then mix vigorously until you have a consistent milky composition. Pour the resulting composition into a suitable container and seal. As it cools, the composition becomes less viscous and forms a creamy liquid. Adding a higher percentage of microcrystalline wax results in a smooth paste that is less viscous. A preferred combination with wide applications as a base composition is 700 parts of natural or synthetic petroleum solvent, to 100 parts of normal paraffin, to 200 parts of melted microcrystalline wax. White oil may be used in place of normal paraffin or isoparaffin to smooth the composition. The percentage combination of ingredients may be varied within the approximate ranges stated, and any natural or synthetic petroleum solvent may be substituted for the example solvent.

EXAMPLE 2

Hand Cream Paint Remover

Starting with 40–750 parts of synthetic isoparaffinic hydrocarbon (odorless mineral spirits) at room temperature, add 10 to 200 parts of normal paraffin, add 1 to 10 parts of aloe oil, add 1 to 10 parts of eucalyptus oil, add 1 to 20 parts of nonionic surfactant and 1 to 20 parts of ionic surfactant and then mix vigorously. Heat microcrystalline wax at approximately 180 to 200 degrees Fahrenheit, until it is completely melted. Pour 200–400 parts of the melted microcrystalline wax into the mixture then stir vigorously until it is evenly mixed. Add 10 to 100 grams of pumice powder per liter and then mix vigorously again. As it cools, the resultant chemical mix becomes less viscous and forms into a gel or hand cream suitable as a hand paint remover for oil based paints, stains, varnish, lacquer or urethane. A preferred composition for use as a hand cream paint remover is 670 parts of odorless mineral spirits, to 100 parts of normal paraffin or isoparaffin, to 5 parts of aloe oil, to 5 parts of eucalyptus oil, to 5 parts of ionic surfactant to 5 parts of nonionic surfactant, to 300 parts of melted microcrystalline wax. Add 20 grams of pumice powder per liter.

There are multiple benefits to the invention which include: reducing the volatility of petroleum solvents, making the solvents less hazardous to handle and the formation of a stable composition as a base stock for the addition of additives that result in unique industrial and home products.

The base composition of 70 parts of synthetic odorless minder spirits, 10 parts of normal paraffin, and 20 parts of melted microcrystalline wax, was tested by an independent testing laboratory to estimate emission rates per start when used as a charcoal lighter. The test was performed in accordance with California's South Coast Air Quality Management District Rule 1174 Ignition Method Compliance Certification Protocol, with the exception that the hydrocarbon results were based upon the continuous hydrocarbon measurements instead of SCAQMD Method 25.1. The Resultant Emission Rate (LB VOC/Start) was 0.0044. The South Coast Air Quality Management District Rule 1174 Limitation is 0.020. These results indicate that the base composition tested was well within the Rule limitations for Volatile Organic Compounds per start. As a comparison, the best known charcoal lighter has a resultant emission rate of 0.018 lb VOC's per start.

Since the base composition with synthetic odorless mineral spirits gives off such a small amount of volatile organic compounds when burned, it can be added to coal particles or coal dust to fluidize the coal. This facilities pumping of the coal, enhances the coal as a fuel source and reduces the volatile organic compounds in emissions.

The base composition with synthetic odorless mineral spirits has significant benefits as a wood stove, wood pellet heater, or fireplace fire starter. The mixture lights easily when applied to carbonaceous materials but does not flare up, due to its low volatility. The mixture is odorless when odorless mineral spirits are used as the solvent. The mixture spreads across the carbonaceous fuel source after lighting. It also burns approximately 50% longer than other plain solvent fire starters, such as charcoal lighter or kerosene.

As a hand paint remover for oil based paint, the composition offers unique benefits over existing hand paint removers. Typical hand paint removers are made with alcohol, which has limited ability to remove oil based paint. When plain solvents are used on the skin, they tend to dry out or de-fat the skin, which can result in dermatitis. The base composition can be combined with skin emollients, such as aloe, others, such as eucalyptus oil (which has an antiseptic quality and pleasing odor), surfactants and pumice powder to result in a cream hand paint remover that is very effective yet is less damaging to the skin than a plain solvent. The mixture is less volatile than a plain solvent, which makes it less of a fire hazard. It has a pleasant odor, and since a small amount is effective, it doesn't present the disposal problems of a plain solvent.

It should be clear at this time that a creamy smooth chemical composition has been provided that is useful in multiple applications. However, the present invention is not to be considered as limited to the examples which are to be considered illustrative rather than restrictive.

I claim:

1. A process for making a chemical composition comprising the steps of:

mixing 200 to 800 parts by volume of liquid petroleum solvent with 10 to 500 parts by volume of normal paraffin or isoparaffin at room temperature to form a liquid paraffin mixture;

heating microcrystalline wax to between 180 and 200 degrees Fahrenheit until melted; and vigorously mixing 90 to 700 parts by volume of the melted microcrystalline wax with said liquid paraffin mixture to form a creamy liquid; and mixing about 1 to 10 parts by volume of aloe oil with the composition to form a cleansing hand cream.

2. The process for making a chemical composition in accordance with claim 1 in which about 700 parts by volume of liquid petroleum solvent is mixed with about 100 parts by volume of normal paraffin or isoparaffin and 200 parts by volume of microcrystalline wax.

3. The process for making a chemical composition in accordance with claim 1 in which about 400 to 800 parts by volume of liquid petroleum solvent is mixed with 10 to 200 parts by volume of normal paraffin or isoparaffin and 150 to 200 parts by volume of microcrystalline wax and further mixing therewith about 1 to 20 parts by volume of a nonionic surfactant.

4. The process for making a chemical composition in accordance with claim 3 in which about 1 to 10 parts by volume of eucalyptus oil is further mixed with the composition.

5. The process for making a chemical composition in accordance with claim 4 in which about 670 parts by volume of liquid petroleum solvent is mixed with about 100 parts by volume of normal paraffin or isoparaffin and about 300 parts by volume of microcrystalline wax which is further mixed with about 5 parts by volume of nonionic surfactant and 5 parts by volume of aloe oil and 5 parts by volume of eucalyptus oil and further mixed with about 20 grams per liter of pumice powder.

6. A chemical composition for use as a cleansing hand cream and paint remover comprising:

a solvent paraffin mixture having 200 to 800 parts by volume of liquid petroleum solvent and 10 to 500 parts by volume of normal paraffin or isoparaffin;

90 to 700 parts by volume of melted microcrystalline wax blended into said paraffin mixture to form a creamy liquid; and 1 to 10 parts by volume of eucalyptus oil mixed with the composition to form a cleansing hand cream.

7. The chemical composition in accordance with claim 6 having about 700 parts by volume of liquid petroleum solvent mixed with about 100 parts by volume of normal paraffin or isoparaffin and 200 to 700 parts by volume of microcrystalline wax.

8. The chemical composition in accordance with claim 6 having 400 to 800 parts by volume of liquid petroleum solvent mixed with 10 to 200 parts by volume of normal paraffin or isoparaffin and 150 to 200 parts by volume of microcrystalline wax and further mixed with about 1 to 20 parts by volume of a nonionic surfactant.

9. The chemical composition in accordance with claim 8 further having about 1 to 10 parts by volume of aloe oil mixed with the composition.

10. The chemical composition in accordance with claim 9 having about 670 parts by volume of petroleum solvent mixed with about 100 parts by volume of normal paraffin or isoparaffin and about 200 parts by volume of microcrystalline wax and about 5 parts by volume of nonionic surfactant and 5 parts by volume of aloe oil and 5 parts by volume of eucalyptus oil and about 20 grams per liter of pumice powder.

\* \* \* \* \*